United States Patent
Mayer et al.

(10) Patent No.: US 9,846,135 B2
(45) Date of Patent: Dec. 19, 2017

(54) MOISTURE SENSOR ARRANGEMENT

(71) Applicant: E+E Elektronik Ges.m.b.H, Engerwitzdorf (AT)

(72) Inventors: Elmar Mayer, Nuβdorf (DE); Georg Niessner, Katsdorf (AT); Joachim Runck, Linz (AT)

(73) Assignee: E+E ELEKTRONIK GES.M.B.H, Engerwitzdorf (AT)

( * ) Notice: Subject to any disclaimer, the term of this patent is extended or adjusted under 35 U.S.C. 154(b) by 308 days.

(21) Appl. No.: 13/868,603

(22) Filed: Apr. 23, 2013

(65) Prior Publication Data
US 2013/0287062 A1 Oct. 31, 2013

(30) Foreign Application Priority Data
Apr. 25, 2012 (DE) .................. 10 2012 008 118

(51) Int. Cl.
G01N 27/22 (2006.01)
H01L 27/04 (2006.01)

(52) U.S. Cl.
CPC .......... *G01N 27/223* (2013.01); *G01N 27/225* (2013.01); *G01N 27/228* (2013.01); *H01L 27/04* (2013.01)

(58) Field of Classification Search
CPC ...... G01N 27/223; G01N 19/10; H01L 27/04; H01L 21/70
USPC .............................. 73/335; 374/142; 257/414
See application file for complete search history.

(56) References Cited

U.S. PATENT DOCUMENTS

| | | | |
|---|---|---|---|
| 5,444,637 A * | 8/1995 | Smesny ................ | B24B 37/013 257/E21.528 |
| 6,249,136 B1 * | 6/2001 | Maley ...................... | 324/754.22 |
| 6,690,569 B1 * | 2/2004 | Mayer .................. | G01N 27/225 361/281 |

(Continued)

FOREIGN PATENT DOCUMENTS

| | | |
|---|---|---|
| DE | 102 25 373 A1 | 4/2003 |
| EP | 1 236 038 B1 | 11/2005 |
| WO | WO 2007/014800 A1 | 2/2007 |

OTHER PUBLICATIONS

Rittersma, Z.M., "Recent Achievements in Miniaturised Humidity Sensors—A Review of Transduction Techniques," Sensors and Actuators A, vol. 96, 2002, pp. 196-210.

(Continued)

*Primary Examiner* — Randy Gibson
*Assistant Examiner* — Gedeon M Kidanu
(74) *Attorney, Agent, or Firm* — Brinks Gilson & Lione

(57) ABSTRACT

A moisture sensor arrangement including a plate-like semiconductor substrate and an integrated signal processing component disposed on a first side of the semiconductor substrate. The moisture sensor arrangement including a capacitive moisture sensor connected electrically conductively to the integrated signal processing component, wherein the capacitive moisture sensor is disposed on either the first side or a second side of the semiconductor substrate that is opposite the first side of the semiconductor substrate. In addition, the plate-like semiconductor substrate includes 1) plated through-holes, by way of which elements on the first side and the second side of the semiconductor substrate are electrically connectable to one another; and 2) a temperature sensor integrated with the integrated signal processing component.

9 Claims, 3 Drawing Sheets

(56) References Cited

U.S. PATENT DOCUMENTS

| | | | |
|---|---|---|---|
| 6,911,392 B2 | 6/2005 | Bieck et al. | |
| 7,154,372 B2* | 12/2006 | Vanha | G01F 15/10 338/22 SD |
| 7,181,966 B2 | 2/2007 | Isogai et al. | |
| 7,222,531 B2* | 5/2007 | Isogai et al. | 73/335.04 |
| 7,340,952 B2* | 3/2008 | Tanida | G01N 27/225 361/286 |
| 2004/0008471 A1* | 1/2004 | Davis | G01N 27/225 361/306.3 |
| 2005/0052437 A1* | 3/2005 | Hudson | G01K 7/015 345/204 |
| 2005/0135465 A1* | 6/2005 | Andrus | H04L 1/0043 375/220 |
| 2006/0048572 A1* | 3/2006 | Isogai | G01N 27/223 73/335.04 |
| 2006/0070449 A1* | 4/2006 | Yokoyama et al. | 73/754 |
| 2006/0238290 A1* | 10/2006 | Arisaka | 338/35 |
| 2007/0107500 A1* | 5/2007 | Patel | 73/73 |
| 2008/0156095 A1* | 7/2008 | Tsuji | B81B 7/0048 73/504.02 |
| 2008/0191716 A1* | 8/2008 | Chen | G01N 27/223 324/665 |
| 2008/0283991 A1 | 11/2008 | Reinert | |
| 2009/0066066 A1* | 3/2009 | Franke | B60R 21/0136 280/735 |
| 2010/0096708 A1 | 4/2010 | Eckstein | |
| 2011/0079649 A1* | 4/2011 | Daamen | G01D 5/14 235/492 |
| 2013/0137259 A1* | 5/2013 | Bieck et al. | 438/612 |

OTHER PUBLICATIONS

Search Report for corresponding European Patent Application 13 16 4715 dated Jul. 2, 2013.

* cited by examiner

MOISTURE SENSOR ARRANGEMENT

RELATED APPLICATIONS

Applicants claim, under 35 U.S.C. §119, the benefit of priority of the filing date of Apr. 25, 2012 of a German patent application, copy attached, Serial Number 10 2012 008 118.9, filed on the aforementioned date, the entire contents of which is incorporated herein by reference.

BACKGROUND

1. Technical Field

The present invention relates to a moisture sensor arrangement.

2. Background Information

From European patent disclosure EP 1 236 038 B1, a sensor arrangement is known which has a sensor, such as a capacitive moisture sensor, on the upper side of a first semiconductor substrate. The capacitive moisture sensor includes two interdigital electrodes placed side-by-side and one dielectric measurement layer which changes its capacitance as a function of moisture. The measurement signals generated in this way are further processed in the semiconductor chip and prepared suitably for transmission to a subsequent electronic unit. This reference provides no further information regarding how the semiconductor chip is electrically contacted or how the sensor arrangement is mounted, such as on a circuit board.

U.S. Pat. No. 7,181,966 B2, the entire contents of which are incorporated herein by reference, discloses a further sensor arrangement which has a sensor, such as a capacitive moisture sensor, on the upper side of a first semiconductor substrate. On the opposite underside of the first semiconductor substrate is a second semiconductor substrate, with a signal processing component disposed on it. The second semiconductor substrate is embodied as a CMOS-ASIC, for instance. An electrically conductive connection between the sensor and the signal processing component is brought about via plated through-holes in the first semiconductor substrate. A disadvantage of this version is that the overall construction of the sensor arrangement requires two semiconductor substrates.

In U.S. Patent Application Publication No. 2011/0079649 A1, the entire contents of which are incorporated herein by reference, a sensor arrangement is proposed in which a sensor, such as a capacitive moisture sensor with interdigital electrodes, is disposed on one side of a semiconductor substrate. A CMOS signal processing component without its own carrier substrate is disposed on the other side of the semiconductor substrate. Here, as well, the sensor and the CMOS signal processing component are electrically conductively connected to one another via plated through-holes in the semiconductor substrate. No details on how the CMOS signal processing component is embodied can be found in this reference.

OBJECTS AND SUMMARY OF THE INVENTION

An object of the present invention is to disclose a moisture sensor arrangement of compact structure that is simple to contact electrically and by way of which reliable measurement of the ambient moisture is possible.

This object is attained according to the present invention by a moisture sensor arrangement that includes a plate-like semiconductor substrate and an integrated signal processing component disposed on a first side of the semiconductor substrate. The moisture sensor arrangement including a capacitive moisture sensor connected electrically conductively to the integrated signal processing component, wherein the capacitive moisture sensor is disposed on either the first side or a second side of the semiconductor substrate that is opposite the first side of the semiconductor substrate. In addition, the plate-like semiconductor substrate includes 1) plated through-holes, by way of which elements on the first side and the second side of the semiconductor substrate are electrically connectable to one another; and 2) a temperature sensor integrated with the integrated signal processing component.

The moisture sensor arrangement of the present invention includes a plate-like semiconductor substrate, an integrated signal processing component which is disposed on one side of the semiconductor substrate, and a capacitive moisture sensor which is connected electrically conductively to the signal processing component and is disposed on either the same or the opposite side of the semiconductor substrate as the signal processing component. The semiconductor substrate has plated through-holes, by way of which elements on opposite sides of the semiconductor substrate are electrically connectable to one another. Furthermore, at least one temperature sensor is integrated with the signal processing component.

The signal processing component can include at least the following further components:
- at least one analog/digital converter unit for reading in and digitizing the analog measurement signals of the moisture sensor and of the temperature sensor;
- an evaluation unit for determining the measured variable from the measurement signals that have been read in; and
- a digital interface unit for serial transmission of the determined measured variable to a downstream subsequent electronic unit.

The signal processing component can for example be embodied as a housingless CMOS layer stack.

It is possible that the capacitive moisture sensor includes at least two electrodes and one moisture-sensitive measurement layer.

The capacitive moisture sensor can be embodied as a plate capacitor having at least one basic electrode and at least one cover electrode, between which the moisture-sensitive measurement layer is disposed.

In one possible variant, the moisture sensor includes a single, two-dimensional basic electrode and a single two-dimensional cover electrode, which are each connected electrically conductively to the signal processing component.

Alternatively, however, it can also be provided that the moisture sensor includes a plurality of two-dimensional basic electrodes and a single two-dimensional cover electrode, and that only the basic electrodes are connected electrically conductively to the signal processing component.

Advantageously, spherical contacting elements are disposed on the opposite side of the semiconductor substrate from the moisture sensor.

It is possible that the moisture sensor arrangement further includes a nonvolatile memory, in which calibration data relating to the temperature sensor, to which the evaluation unit has access for temperature determination, are stored.

In one embodiment, it can be provided that the moisture sensor is disposed vertically above the signal processing component, and via the plated through-holes in the semiconductor substrate, the signal processing component is connected electrically conductively to contacting elements on the opposite side of the semiconductor substrate.

In one embodiment, the integrated signal processing component includes: 1) an analog/digital converter unit for reading in and digitizing analog measurement signals of the capacitive moisture sensor and the temperature sensor; 2) an evaluation unit for determining a measured variable from the analog measurement signals that have been read in; and 3) a digital interface unit for serial transmission of the determined measured variable to a downstream subsequent electronic unit, wherein, via the plated through-holes, energy supplied to the integrated signal processing component and serial transmission of the measured variable to said downstream subsequent electronic unit are effected.

In a further embodiment, it can be provided that the signal processing component, on its side toward the moisture sensor, has an insulation layer, on which the at least one basic electrode is disposed; the moisture-sensitive measurement layer of the moisture sensor is disposed above the basic electrode; and the cover electrode of the moisture sensor is disposed above the moisture-sensitive measurement layer.

The moisture sensor is disposed on either a first side or a second side of the semiconductor substrate and the integrated signal processing component is disposed on another one of the first side or the second side of said semiconductor substrate and wherein the moisture sensor and the integrated signal processing component are connected electrically conductively to one another via the plated through-holes.

Via the plated through-holes in the semiconductor substrate, the transmission of the analog measurement signals of the moisture sensor to the signal processing component can be accomplished.

One resultant advantage of the moisture sensor arrangement of the present invention is an extremely compact structure. The electrical contacting of the moisture sensor arrangement requires no bond wires, and thus the space the signal processing component requires is reduced to its own external dimensions. An additional housing for protecting the bond wires can be dispensed with as well, which also proves favorable with regard to requiring only little space. Moreover, nearly the entire surface area of the signal processing component can be used for the moisture sensor, and as a result, greater precision of the moisture sensor arrangement of the present invention can be attained.

Integrating the temperature sensor with the signal processing component moreover ensures that the temperature measurement required for moisture determination is done at an ideal distance from the measurement point where the capacitance is measured.

Further advantages and details of the present invention will become apparent from the ensuing description of exemplary embodiments in conjunction with the drawings.

DETAILED DESCRIPTION OF THE PREFERRED EMBODIMENTS

Figure 1:
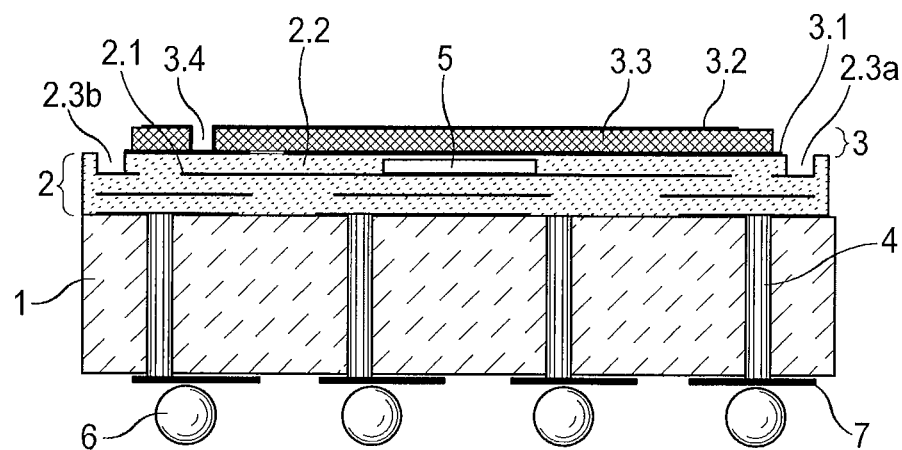
FIG. 1 is a lateral sectional view of a first exemplary embodiment of a moisture sensor arrangement in accordance with the present invention.

In FIG. 1, a first exemplary embodiment of a moisture sensor arrangement of the present invention is shown highly schematically.

Figure 5:
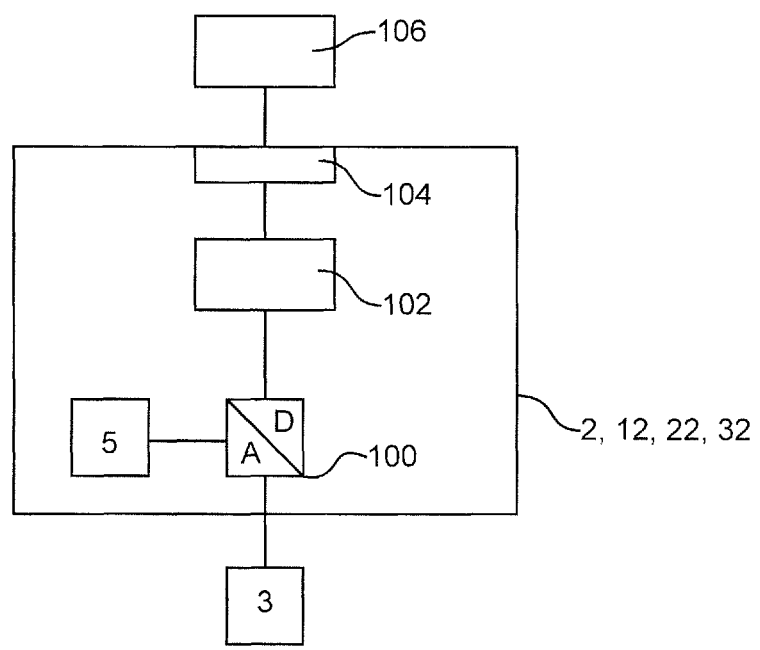
FIG. 5 is a top schematic view of an embodiment of an arrangement of electronic components for the signal processing components of FIGS. 1-4.

The moisture sensor arrangement of the present invention includes a plate-like semiconductor substrate 1, such as a silicon substrate, on which the various elements of the moisture sensor arrangement are placed. In the first exemplary embodiment shown in FIG. 1, an integrated signal processing component 2 is disposed on the top side of the semiconductor substrate 1. The signal processing component 2 is constructed as a housingless CMOS layer stack, with which various electronic components for signal processing and signal preparation are integrated. A capacitive moisture sensor 3 is in turn disposed above the signal processing component 2, that is, vertically adjacent to the signal processing component 2. The moisture sensor 3 is electrically conductively connected to the signal processing component 2. The analog measurement signals generated by the moisture sensor 3 are processed in the signal processing component 2, and in particular, the measured variable sought, which is "relative moisture," is determined by the signal processing component 2 from the measurement signals, and the measured variable is prepared for serial transmission to a downstream subsequent electronic unit. Hereinafter, with regard to the measured variable, only the term "moisture" for the measured variable will be used. To accomplish this kind of signal processing, the signal processing component 2 includes, as an integrated electronic component, an analog/digital converter unit 100, which serves to read in and digitize the analog measurement signals of the moisture sensor 3. Such an integrated electronic component of the signal processing component 2 is shown schematically in FIG. 5, wherein the drawing is not limited to the orientation and/or sizes of the various components shown. As a further electronic component, an evaluation unit 102 in the signal processing component 2 is also provided, which ascertains the measured variable "moisture" from the measurement signals of the moisture sensor 3. Finally, as a further electronic component, a suitably embodied interface unit 104 is provided, which serves the purpose of serial transmission of the variable measured by the moisture sensor 3 to a subsequent electronic unit 106.

In addition to these electronic components—which are not shown in detail—according to the present invention a temperature sensor 5, schematically indicated in FIG. 1, is integrated with the signal processing component 2. The temperature sensor 5 furnishes measured variables relating to the ambient temperature, which is used by the evaluation unit of the signal processing component 2, along with the measurement signals of the moisture sensor 3, for precise determination of the measured variable "moisture." Disposing the moisture sensor 3 and temperature sensor 5 adjacent one another in the moisture sensor arrangement of the invention makes especially good determination of the measured variable "moisture" possible.

The temperature determination is effected here via the evaluation unit of the signal processing component 2. To that end, the band gap voltage of the semiconductor material of the temperature sensor 5 is delivered, digitized via the aforementioned analog/digital converter unit, to the evaluation unit. Alternatively, a further analog/digital converter unit could be provided for that purpose in the moisture sensor arrangement of the present invention.

For high-precision determination of the measured variable "moisture," it also proves advantageous if the temperature value is calibrated afterward. To that end, the moisture sensor arrangement of the present invention has a nonvolatile memory, in which calibration data about the temperature sensor are stored, and the evaluation unit accesses such data for the temperature determination.

The signal processing component 2 embodied as a CMOS layer stack has in the direction of the moisture sensor 3 a final metalizing layer 2.1, which functions as a shielding layer and minimizes possible impairment of the signal processing by the moisture sensor 3 in the signal processing component 2. In the signal processing component 2, an insulation layer 2.2, which may be embodied as a SiN layer or as a $SiO_2$ layer, for example, is also disposed above the final metalizing layer 2.1. The insulation layer 2.2 ensures electrical insulation of the signal processing component 2 from the moisture sensor 3 disposed above it.

A two-dimensional basic electrode 3.1 of the capacitive moisture sensor 3 is disposed above the insulation layer 2.2 of the signal processing component 2. Above the insulation layer 2.2 is a moisture-sensitive measurement layer 3.3, and above the measurement layer 3.3 is a two-dimensional cover electrode 3.2. The basic electrode 3.1, 3.2 here includes nickel/chromium and gold; alternatively, aluminum would be usable in combination with an insulation layer of quartz or SiN. Chromium is contemplated as the material for the cover electrode 3.2. A suitable dielectric, such as polyimide, serves as the measurement layer 3.3, the capacitance of which varies as a function of moisture.

In the present first exemplary embodiment of the moisture sensor arrangement of the present invention, the capacitive moisture sensor 3 is accordingly embodied as a plate capacitor, which includes two two-dimensional electrodes in the form of one basic and one cover electrode 3.1, 3.2, between which the moisture-sensitive measurement layer 3.3 is disposed.

In an alternative embodiment to this, it would in principle be possible to embody the electrodes of the capacitive moisture sensor as interdigital electrodes embodied in finger-like fashion, above which the moisture-sensitive measurement layer is then disposed.

The moisture sensor 3, or in this exemplary embodiment its basic electrode 3.1 and its cover electrode 3.2, are connected electrically conductively to the signal processing component 2. The basic electrode 3.1 disposed on the insulation layer 2.2 of the CMOS layer stack is connected, in the example shown, to the signal processing component 2 via the first contacting region 2.3a, shown on the far right in FIG. 1. In other words, base electrode 3.1 extends into contacting region 2.3a. Thus, base electrode 3.1 is electrically connected with the signal processing component 2 via contacting region 2.3a. For electrically conductively connecting the cover electrode 3.2 to the signal processing component 2, the measurement layer 3.3 has an opening 3.4, by way of which a connection can be made to a second contacting region 2.3b of the signal processing component 2 via another electrode disposed on the insulation layer 2.2.

The semiconductor substrate 1 moreover has a plurality of plated through-holes 4, in the form of cylindrical openings between the top side and the underside, by way of which elements on the opposite sides of the semiconductor substrate 1 can be connected electrically conductively to one another. To that end, a suitable electrically conductive material, such as aluminum or copper, is disposed in the plated through-holes 4.

In the first exemplary embodiment of the moisture sensor arrangement of the present invention, a plurality of spherical contacting elements 6 are disposed on the underside of the semiconductor substrate 1. Via the contacting elements 6, the moisture sensor arrangement shown can be disposed on a carrier element, such as a circuit board.

Via the plated through-holes 4, in the first exemplary embodiment shown, the signal processing component 2 on the top side of the semiconductor substrate 1 is thus connected electrically to the contacting elements 6 on the underside of the semiconductor substrate. Via the plated through-holes 4, the energy supplied to the signal processing component 2 and the serial transmission of the measured variable is thus accomplished concretely from the signal processing component 2 to a subsequent electronic unit—not shown—in which this measured variable can be further utilized.

In the exemplary embodiment shown, the contacting elements 6 are not connected directly to the plated through-holes 4. In particular, on the underside of the semiconductor substrate 1 an electrically conductive rewiring layer 7 is additionally provided as well, and by way of it the position of the contacting elements 6 can be suitably fixed.

The moisture sensor arrangement of the present invention can thus be electrically contacted without requiring bond wires to do so. The contacting elements 6, disposed exclusively on the underside of the semiconductor substrate 1, make automated SMD assembly during further processing possible.

Figure 2:
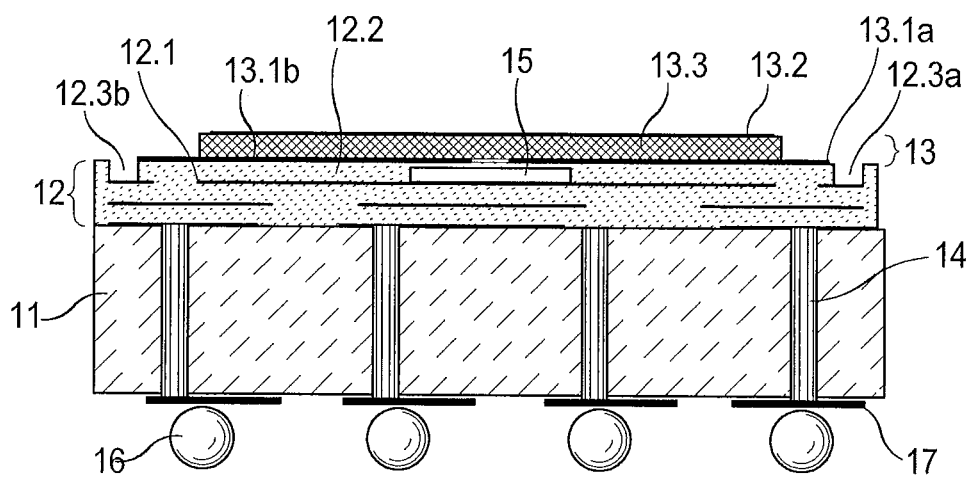
FIG. 2 is a lateral sectional view of a second exemplary embodiment of a moisture sensor arrangement in accordance with the present invention.

A second exemplary embodiment of the moisture sensor arrangement of the present invention is shown in FIG. 2, again in a highly schematic sectional view. Since the structures of the moisture sensor arrangements of FIGS. 1 and 2 are similar, only the definitive differences from the first exemplary embodiment described above will be explained below.

These differences essentially include a somewhat modified embodiment of the capacitive moisture sensor 13. In the first exemplary embodiment of FIG. 1, the capacitive moisture sensor 3 includes a single two-dimensional basic electrode 3.1 and a single two-dimensional cover electrode 3.2, each electrically conductively connected to the signal processing component 2. In a distinction from that, in the second exemplary embodiment of FIG. 2, it is now provided that a plurality of two-dimensional basic electrodes 13.1a, 13.1b are to be disposed on the insulation layer 13.2 of the signal processing component 13. Above them, as in the first example, a moisture-sensitive measurement layer 13.3 and a single two-dimensional cover electrode 13.2 are disposed. Here, only the plurality of basic electrodes 13.1a, 13.1b are connected electrically conductively to the signal processing component 12, via the contacting regions 12.3a, 12.3. Because it is unnecessary to provide contacting for the cover electrode 13.2, an opening in the measurement layer 13.3 that is required in the first example (see item 3.4 of FIG. 1), and the requisite structuring of the cover electrode in that example, are dispensed with. It should be pointed out that the structures and functions performed by the semiconductor substrate 11, plurality of plated through-holes 14, plurality of spherical contacting elements 16 and electrically conductive rewiring layer 17 is similar to that for the semiconductor substrate 1, plurality of plated through-holes 4, plurality of spherical contacting elements 6 and electrically conductive rewiring layer 7, respectively, of FIG. 1.

Figure 3:
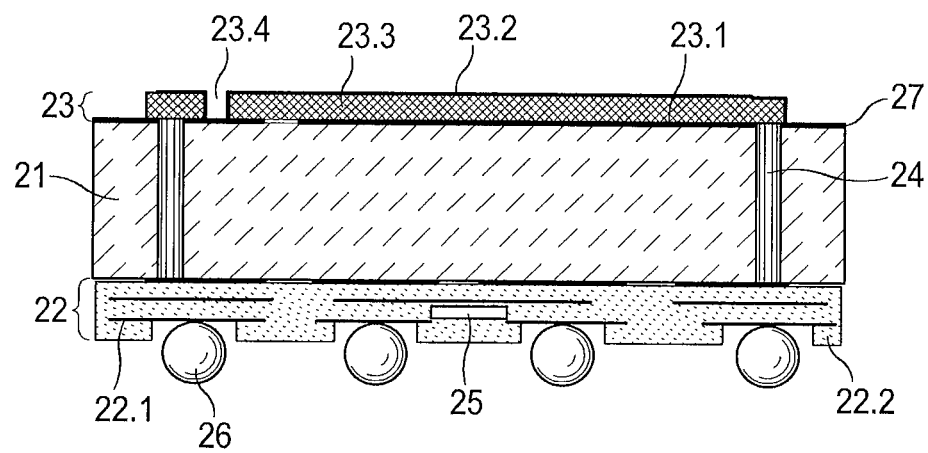
FIG. 3 is a lateral sectional view of a third exemplary embodiment of a moisture sensor arrangement in accordance with the present invention.

A third exemplary embodiment of the moisture sensor arrangement of the present invention is shown schematically in a lateral side view in FIG. 3. For this example, too, only the definitive differences from the foregoing variants of FIGS. 1 and 2 will be explained.

In this example, it is provided that the capacitive moisture sensor 23 and the signal processing component 22 are disposed on opposite sides of the semiconductor substrate 21. The moisture sensor 23, with a two-dimensionally embodied basic electrode 23.1, is disposed on the top side of the semiconductor substrate 21. In addition, a moisture-sensitive measurement layer 23.3 is disposed above the basic electrode 23.1, and a cover electrode 23.2 closes off the arrangement at the top of the measurement layer 23.3. Between the basic electrode 23.1 and the top side of the semiconductor substrate 21, in the example shown in FIG. 3, an electrically conductive rewiring layer 27 is disposed as well. By way of this rewiring layer 27, the electrically conductive connection of the basic electrode 23.1 and the cover electrode 23.2 with the plated through-holes 24 in the semiconductor substrate 21 can be adapted flexibly. In principle, in the moisture sensor arrangement of the present invention, such a rewiring layer 27 is not absolutely necessary.

In this embodiment, the signal processing component 22 is disposed on the opposite side of the semiconductor substrate 21, that is, on its underside. As in the first two exemplary embodiments of FIGS. 1 and 2, this signal processing component 22 has not only various electronic components, but also a temperature sensor 25 integrated with them. Its measurement signals, together with the measurement signals of the capacitive moisture sensor 23, are used in the signal processing component for ascertaining the measured variable "moisture".

The concrete embodiment of the capacitive moisture sensor with only a single two-dimensional basic electrode 23.1 and a single two-dimensional cover electrode 23.2 and the electrical connection of the two electrodes 23.1, 23.2 to the signal processing component 23 are similar to the first exemplary embodiment described with respect to FIG. 1. As with the embodiment of FIG. 1, a suitable opening 23.4 in the moisture-sensitive measurement layer 23.3 should be provided in order to provide contacting for the cover electrode 23.2.

In this exemplary embodiment, the analog measurement signals of the moisture sensor 23 are accordingly transmitted to the signal processing component 22 via the plated through-holes 24 in the semiconductor substrate 21.

The spherical contacting elements 26 here are again provided on the underside of the semiconductor substrate 21, on which the signal processing component 22 is also located. As can be seen from FIG. 3, the contacting elements 26 here are provided at locations where portions of the insulation layer 22.2 of the signal processing component 22 have been removed, and where the contacting elements 26 are connected electrically conductively to the final metalizing layer 22.1.

This variant of the moisture sensor arrangement of the present invention proves to be advantageous with regard to the least possible mutual influence of the moisture sensor 23 and the signal processing component 22. These components, because of disposition on opposite sides of the semiconductor substrate 21 as provided, are spaced apart by a markedly greater distance than in the two foregoing exemplary embodiments of FIGS. 1 and 2, so that particular the thermal influence of the moisture sensor 23 that is due to the waste heat of the signal processing component 22 can be minimized.

A further advantage of this variant is that in this way the complexity and expense of producing the moisture sensor arrangement can be reduced, since standard methods for mounting the contacting elements 26 for electrical contacting can be employed, as is known for instance for so-called flip-chip ASICs.

Figure 4:
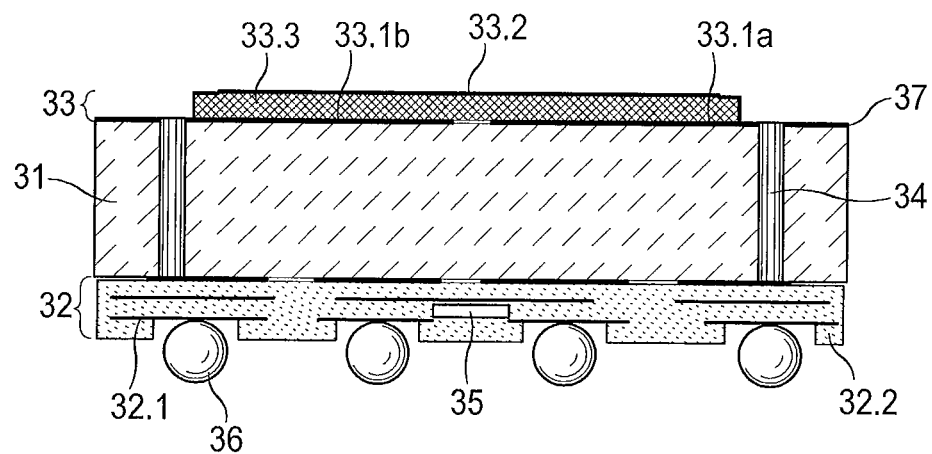
FIG. 4 is a lateral sectional view of a fourth exemplary embodiment of a moisture sensor arrangement in accordance with the present invention.

A fourth exemplary embodiment of the moisture sensor arrangement of the present invention is shown in a schematic sectional view in FIG. 4.

With regard to the disposition of the moisture sensor 33 and the signal processing component 32 on opposite sides of the semiconductor substrate 31, this variant is similar to the third exemplary embodiment of FIG. 3. Only the capacitive moisture sensor 33 is embodied differently. As in the second exemplary embodiment of FIG. 2, once again two basic electrodes 33.1*a*, 33.1*b* are provided, which are electrically conductively connected to the signal processing component 32 via the plated through-holes 34. Conversely, the cover electrode 33.2 disposed above the measurement layer 33.3 is not contacted electrically. Otherwise, the fourth exemplary embodiment of the moisture sensor arrangement of the present invention is similar to the preceding example of FIG. 3.

The foregoing description is provided to illustrate the present invention, and is not to be construed as a limitation. Numerous additions, substitutions and other changes can be made to the invention without departing from its scope as set forth in the appended claims.

We claim:

1. A moisture sensor arrangement, comprising:
   a plate-like semiconductor substrate;
   an integrated signal processing component arranged juxtaposed to a first side of said semiconductor substrate, wherein said integrated signal processing component is embodied as a CMOS layer stack and wherein said integrated signal processing component comprises:
      an analog/digital converter unit for reading in and digitizing analog measurement signals of a capacitive moisture sensor and a temperature sensor;
      an evaluation unit for determining a measured variable from said analog measurement signals that have been read in;
      a digital interface unit for serial transmission of said determined measured variable to a downstream subsequent electronic unit;
   a nonvolatile memory, in which calibration data relating to said temperature sensor to which said evaluation unit has access for temperature determination are stored;
   wherein said capacitive moisture sensor comprises:
      a plate capacitor consisting essentially of:
         a single two-dimensional basic electrode extending along a single plane; and
         a two-dimensional cover electrode facing said single two-dimensional basic electrode; and
      a moisture-sensitive measurement layer disposed between said single two-dimensional basic electrode and said two-dimensional cover electrode, and
   wherein said capacitive moisture sensor is connected electrically conductively to said integrated signal processing component, wherein said capacitive moisture sensor is disposed on either said first side or a second side of said semiconductor substrate that is opposite said first side of said semiconductor substrate, wherein said plate-like semiconductor substrate comprises:

plated through-holes, by way of which elements on said first side and said second side of said semiconductor substrate are electrically connectable to one another; and said temperature sensor, wherein said temperature sensor is integrated with said integrated signal processing component.

2. The moisture sensor arrangement according to claim 1, further comprising spherical contacting elements disposed on either 1) said first side of said semiconductor substrate when said capacitive moisture sensor is disposed on said second side of said semiconductor substrate or 2) said second side of said semiconductor substrate when said capacitive moisture sensor is disposed on said first side of said semiconductor substrate.

3. The moisture sensor arrangement according to claim 1, wherein via said plated through-holes, transmission of said analog measurement signals of said moisture sensor to said integrated signal processing component is accomplished.

4. The moisture sensor arrangement according to claim 1, wherein said capacitive moisture sensor is disposed vertically above said integrated signal processing component, and via said plated through-holes, said integrated signal processing component is connected electrically conductively to contacting elements on said second side of said semiconductor substrate.

5. The moisture sensor arrangement according to claim 4, wherein via said plated through-holes, energy supplied to said integrated signal processing component and serial transmission of said measured variable to said downstream subsequent electronic unit are effected.

6. The moisture sensor arrangement according to claim 4, wherein said integrated signal processing component comprises an insulation layer, on a side of said integrated signal processing component facing toward said capacitive moisture sensor, on which said single two-dimensional basic electrode is disposed, wherein said moisture-sensitive measurement layer is disposed above said single two-dimensional basic electrode, and said two-dimensional cover electrode is disposed above said moisture-sensitive measurement layer.

7. The moisture sensor arrangement according to claim 1, wherein said integrated signal processing component is disposed on another one of said first side or said second side of said semiconductor substrate and wherein said moisture sensor and said integrated signal processing component are connected electrically conductively to one another via said plated through-holes.

8. The moisture sensor arrangement according to claim 7, wherein, via said plated through-holes, transmission of said analog measurement signals of said capacitive moisture sensor to said integrated signal processing component is effected.

9. The moisture sensor arrangement according to claim 7, wherein via said plated through-holes, transmission of analog measurement signals of said moisture sensor to said integrated signal processing component is accomplished.

* * * * *